Figure 3:
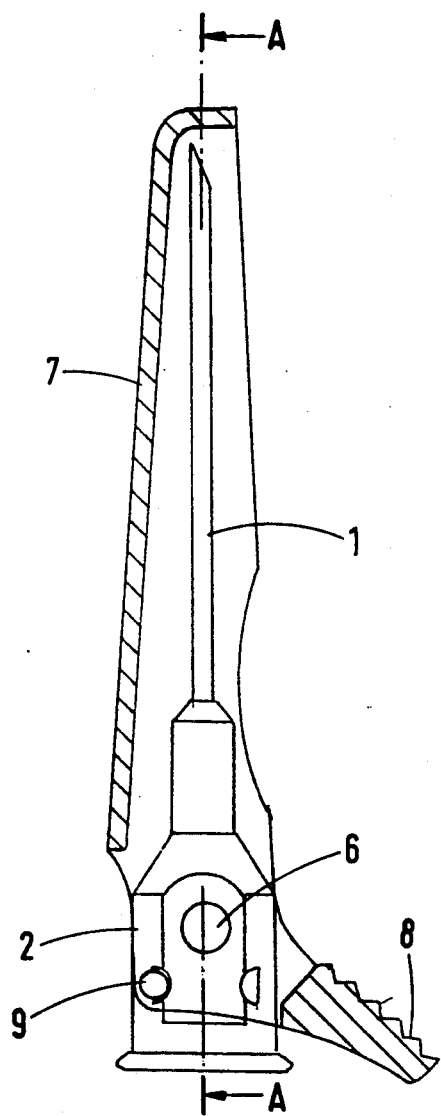

United States Patent [19]

Olliffe

[11] Patent Number: 5,135,509
[45] Date of Patent: Aug. 4, 1992

[54] HYPODERMIC SYRINGE

[76] Inventor: Robert M. Olliffe, 1 The Betchworth Reigate Road, Betchworth Surrey, England

[21] Appl. No.: 640,298
[22] PCT Filed: Jul. 20, 1989
[86] PCT No.: PCT/GB89/00837
 § 371 Date: Jan. 24, 1991
 § 102(e) Date: Jan. 24, 1991
[87] PCT Pub. No.: WO90/01348
 PCT Pub. Date: Feb. 22, 1990

[30] Foreign Application Priority Data

Jul. 29, 1988 [GB] United Kingdom ............. 8818162

[51] Int. Cl.$^5$ .................................... A61M 5/32
[52] U.S. Cl. ............................ 604/192; 604/263
[58] Field of Search ................ 604/192, 263, 187

[56] References Cited

U.S. PATENT DOCUMENTS 3,658,061 4/1972 Hall .......................... 128/214.4
4,681,567 7/1987 Masters et al. .............. 604/198
4,747,836 5/1988 Luther ......................... 604/198
4,820,277 4/1989 Norelli ......................... 604/192

FOREIGN PATENT DOCUMENTS 8705966 6/1987 Fed. Rep. of Germany .
1098727 8/1955 France .
2618685 2/1989 France .
8707162 12/1987 PCT Int'l Appl. .

Primary Examiner—John D. Yasko
Attorney, Agent, or Firm—Ronald P. Kananen

[57] ABSTRACT

A hypodermic syringe is described in which the needle (1) is protected by a guard. The guard includes a needle shroud (7) which is pivotable between open and closed positions and includes releasable locking means (9, 10, 12, 26, 31, 42, 43 and 44) to hold the guard respectively in open and closed positions. An operating arm (8) is attached to the needle shroud (7) to facilitate pivoting of the shroud form the open to the closed positions. Generally, shroud (7) is integrally moulded with arm (8) and needle boss (25) or with a sleeve (24) which can be fitted over boss (25).

7 Claims, 13 Drawing Sheets

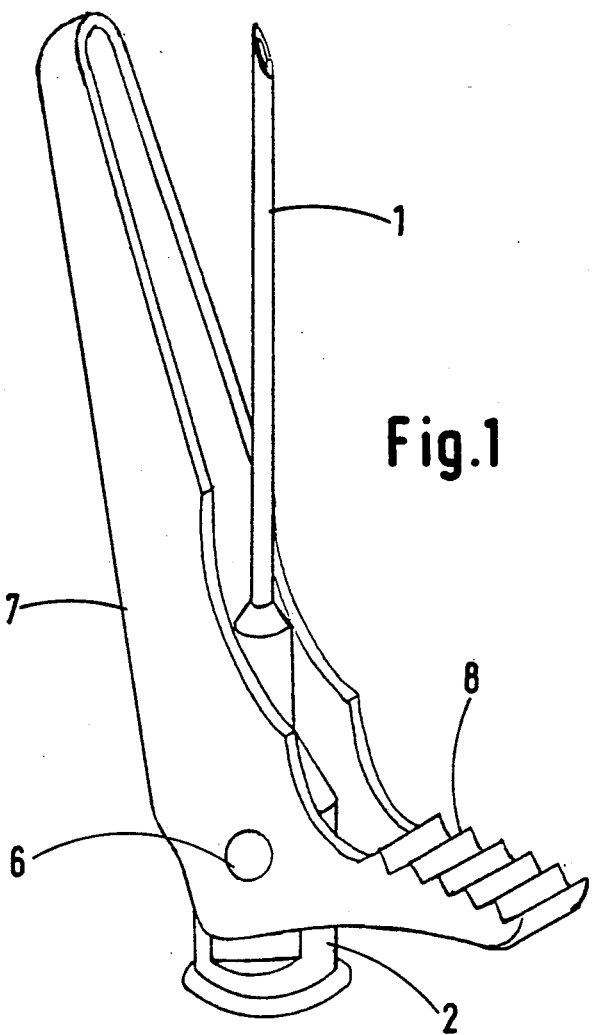
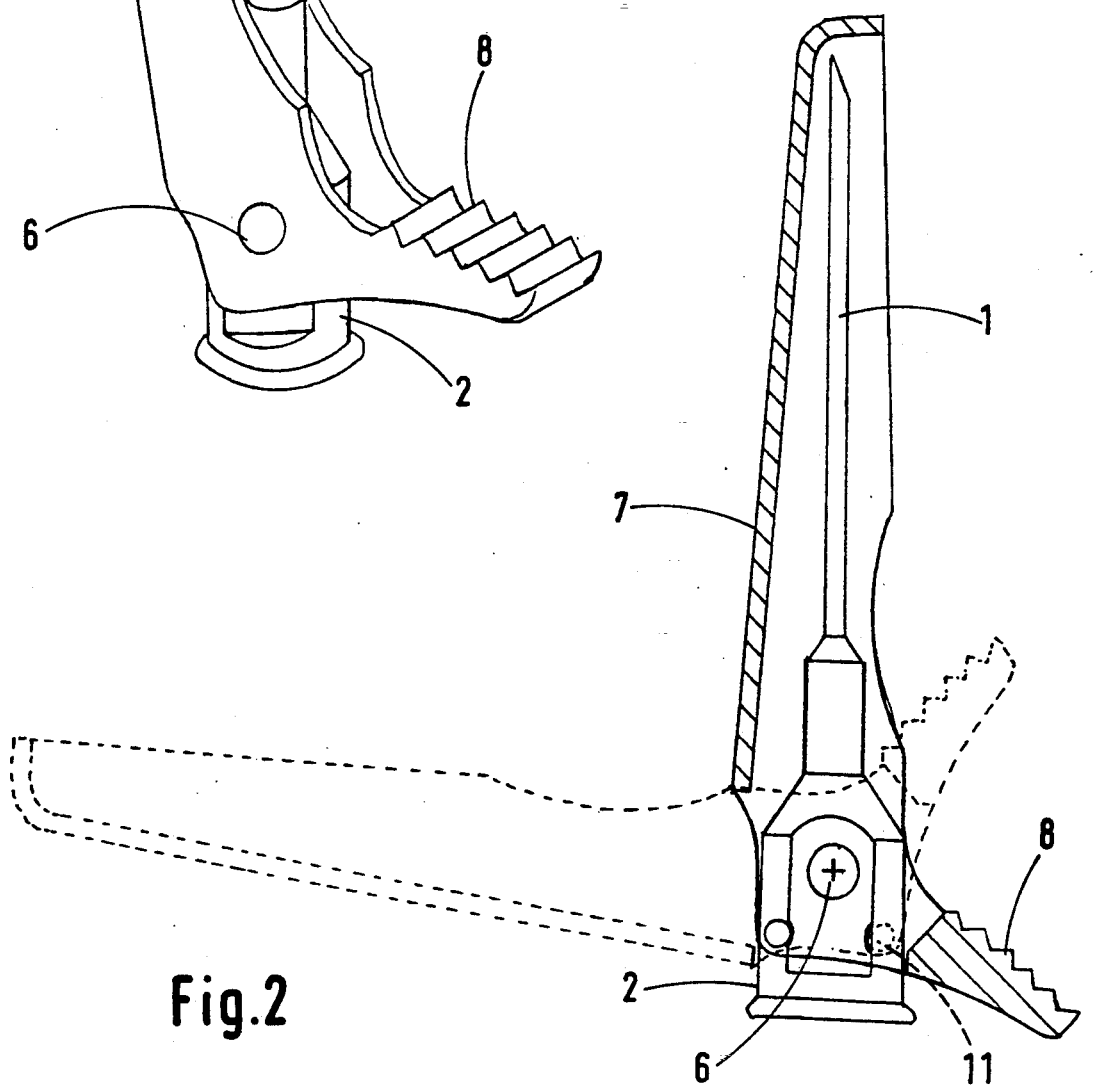

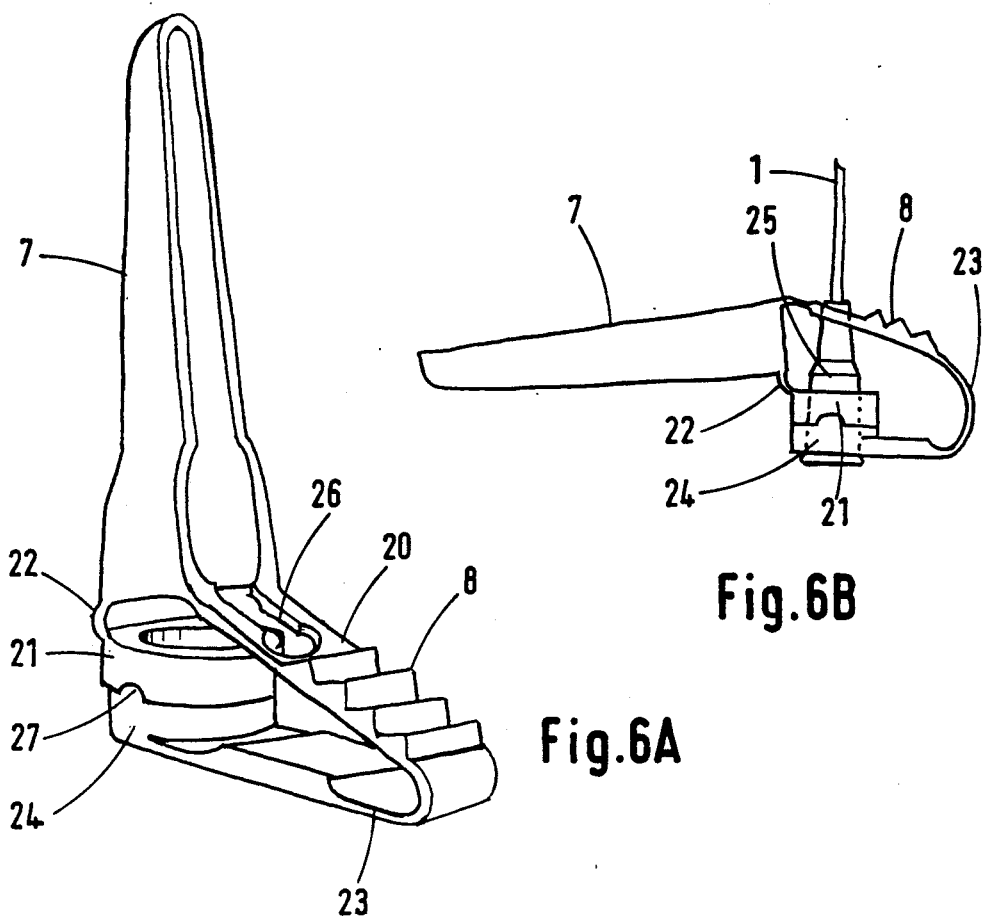
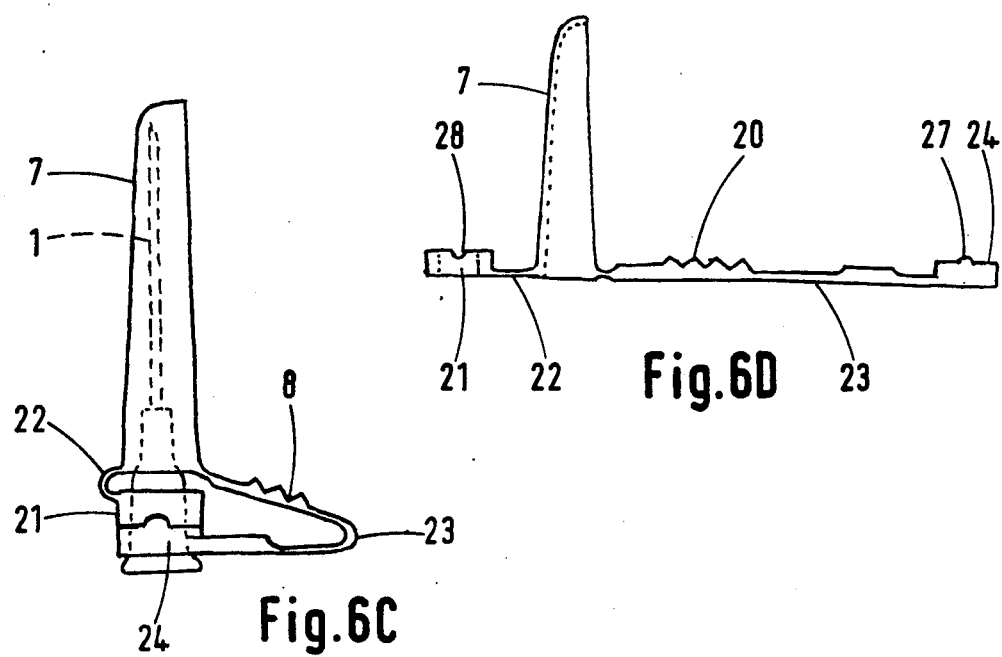

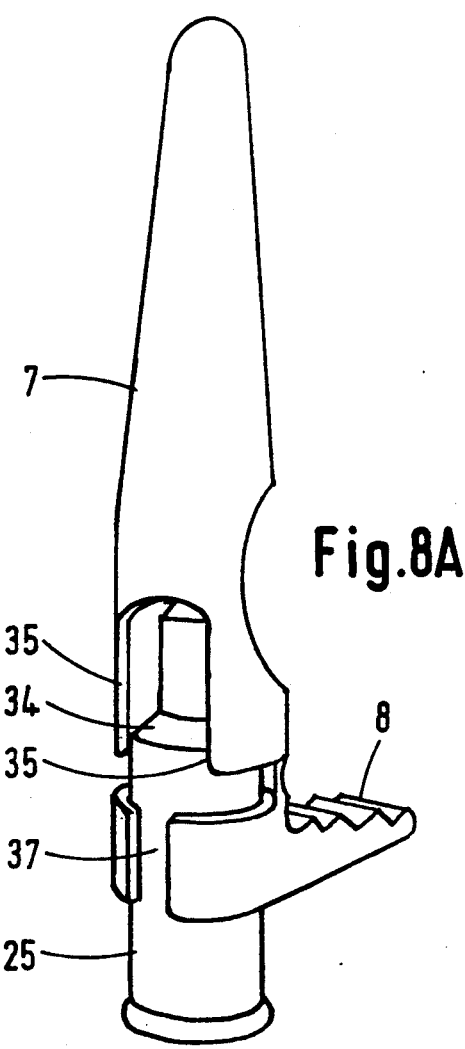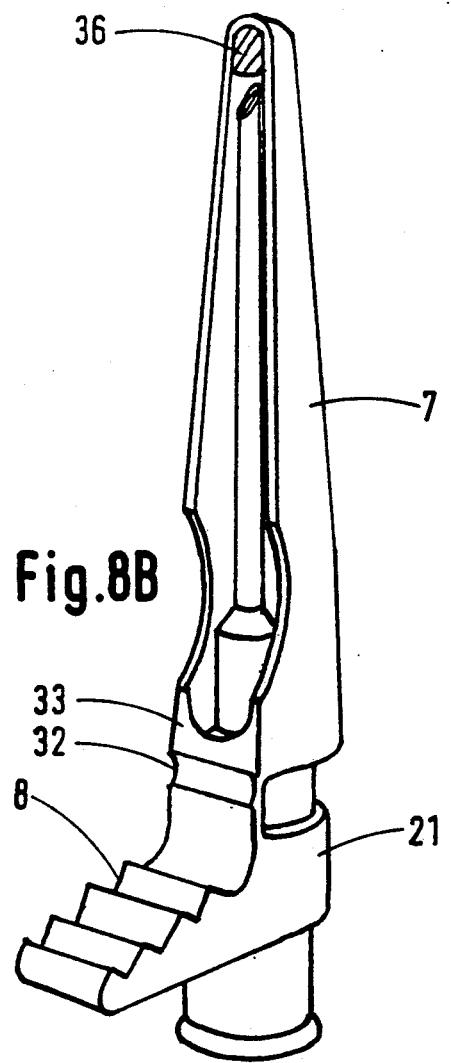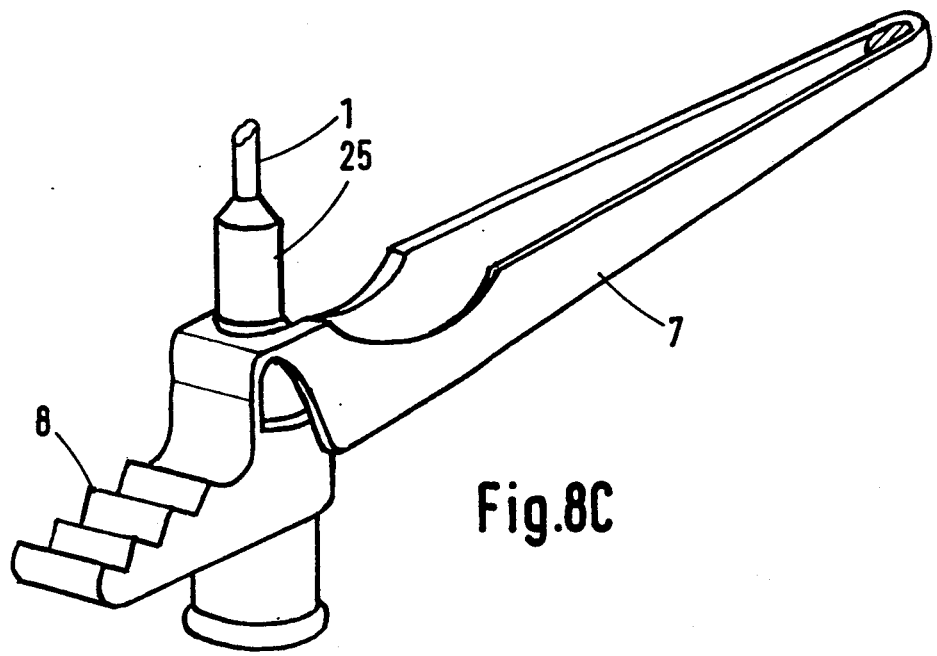

Figure 4:
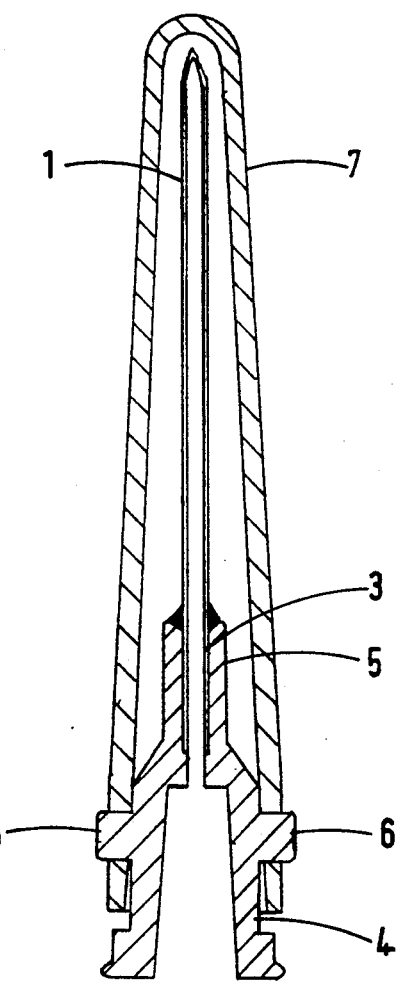

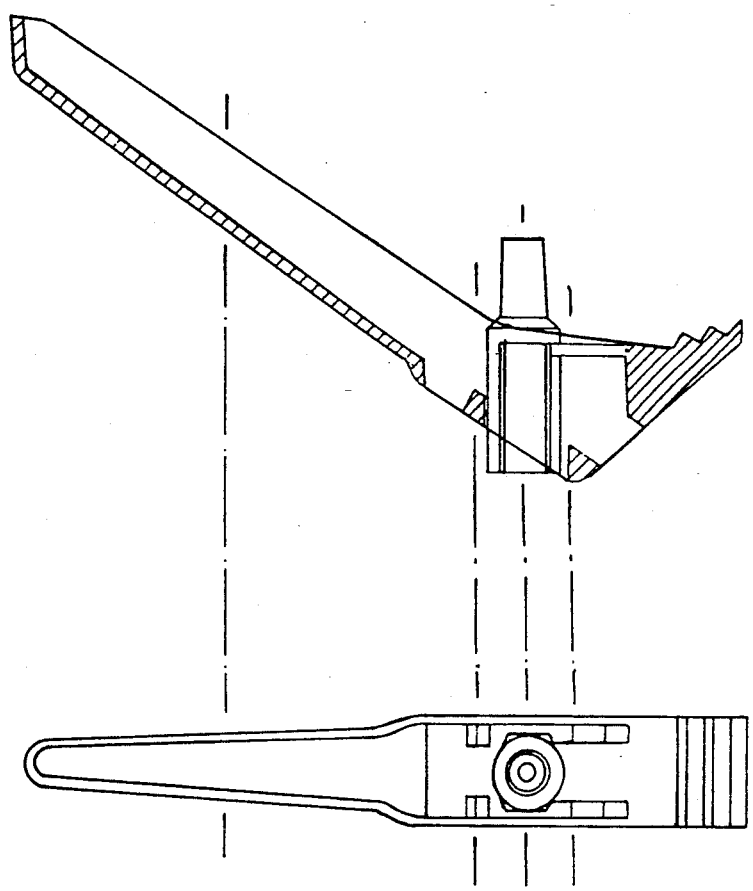
Fig.9N
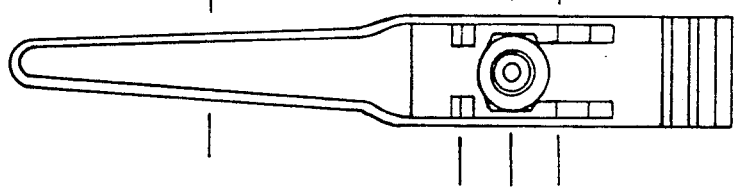
Fig.9P
Fig.9N1
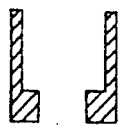
Fig.9N2
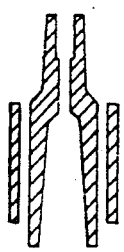
Fig.9N3
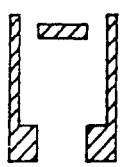
Fig.9N4

HYPODERMIC SYRINGE

This invention relates to hypodermic syringes and in particular provides a syringe which is safe in use.

Because of the growing prevalence of serious diseases which are spread by contact with infected blood, e.g. infectious hepatitis and human immunodeficiency virus (HIV), it is important to dispose safely of hypodermic syringes after use. Conventional practice is to supply needles separately packaged in a sealed tubular sheath. The needle can then be screwed onto a standard syringe barrel and the sheath removed to expose the needle for use.

After the injection has been given or the sample taken from the patient, the sheath is often replaced on the needle and the whole syringe placed in a disposal box for destruction. Unfortunately, the person administering the injection may accidentally touch the end of the needle, particularly when attempting to replace the sheath.

There is consequently a need to provide a safer method of protecting the needles of syringes, particularly after use.

According to the present invention, there is provided a hypodermic syringe having a needle guard which is pivotable between a first position in which it covers the tip of the needle and a second position in which the needle tip is exposed and the guard lies in a position which does not interfere with the use of the syringe.

Normally, the guard will include locking means for releasably holding it in said first and/or second positions. Particularly, when the guard is manufactured in a plastic material, such locking means preferably includes projections or recesses which engage corresponding recesses or projections formed in the base support for the needle or the needle boss.

Pivoting the needle guard between the second and first positions is conveniently achieved by application of finger pressure to a lever extension arm of the guard.

The needle guard is preferably moulded together with its operating arm and the needle boss of the syringe as a single entity or with a fitting, such as a sleeve, which can be slid over a standard needle boss.

Further features and advantages of the syringe of the present invention will become apparent from the following description and accompanying drawings in which:

FIG. 1 is a perspective view of one embodiment of a hypodermic syringe needle fitted with a guard in accordance with the invention.

Figure 5:
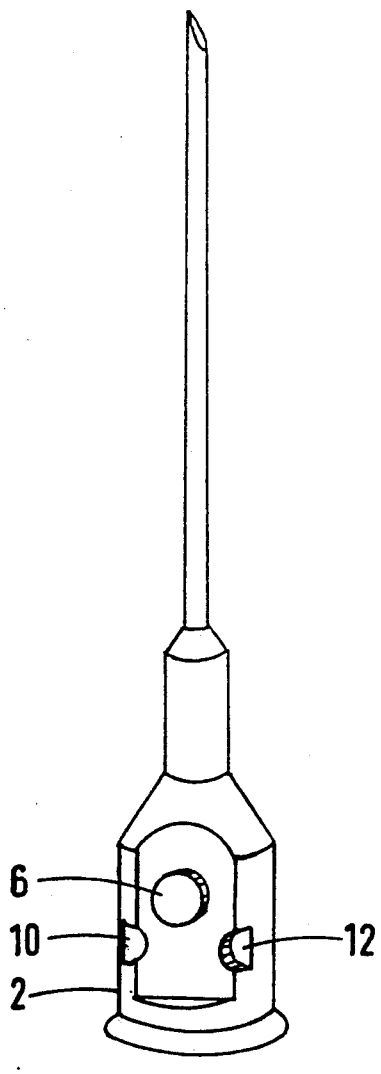
Figure 5A:
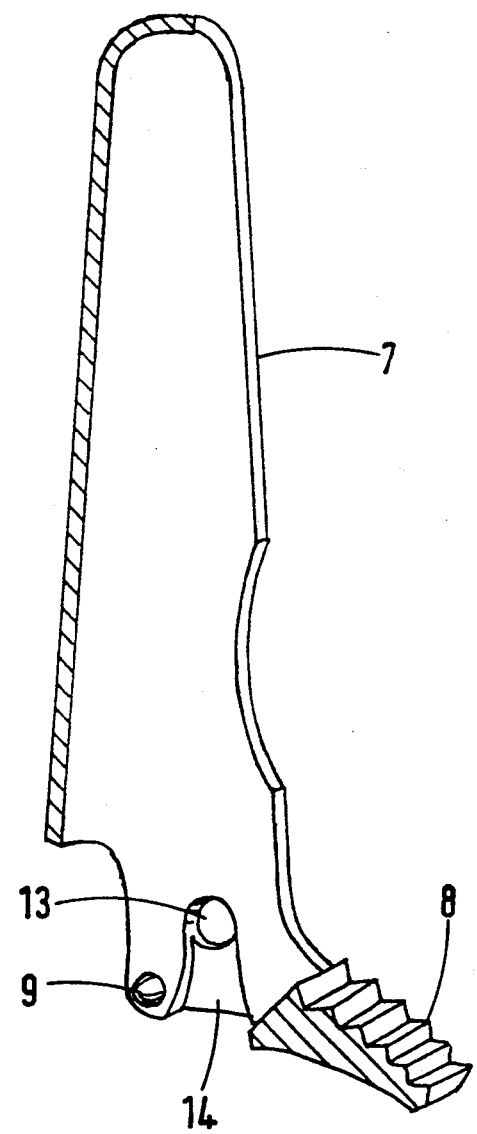
Figure 7A:
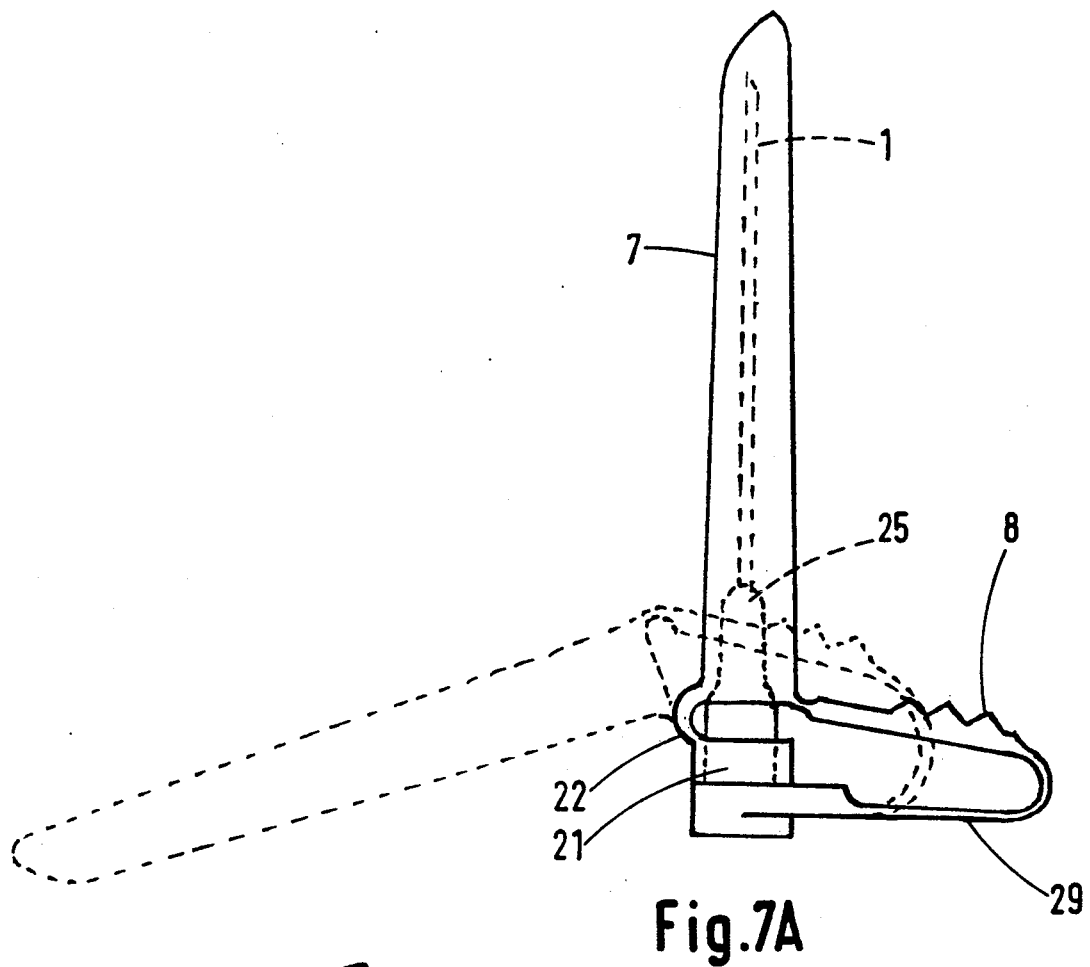
Figure 7B:
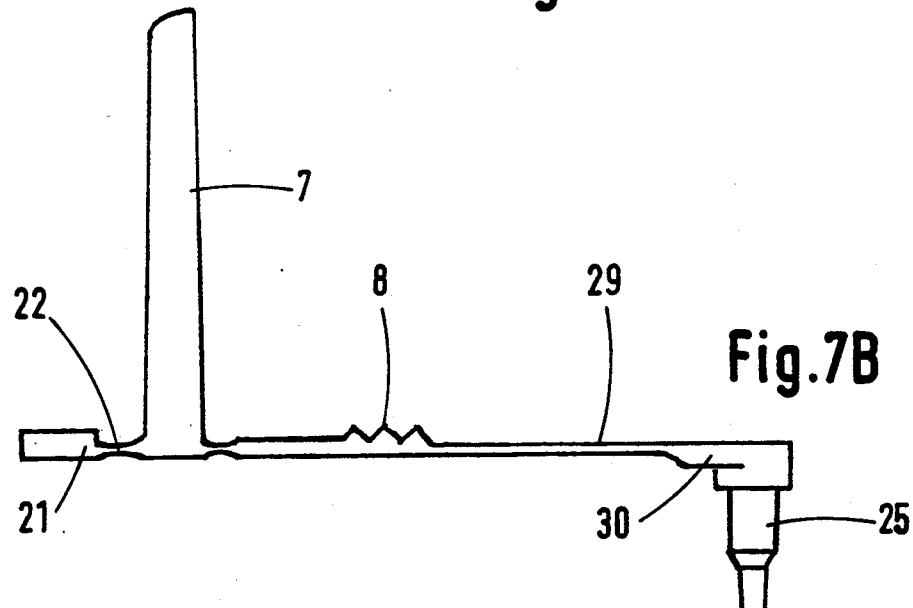
Figure 7C:
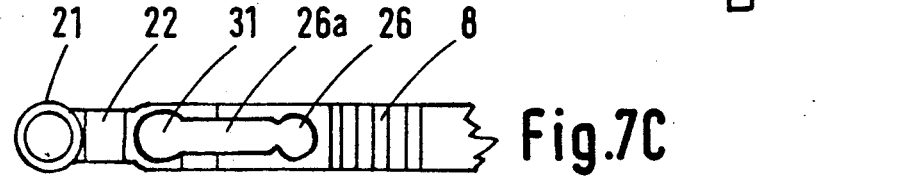
Figure 8D:
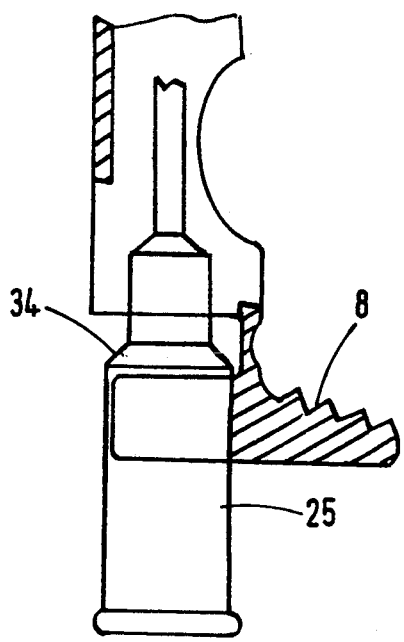
Figure 8E:
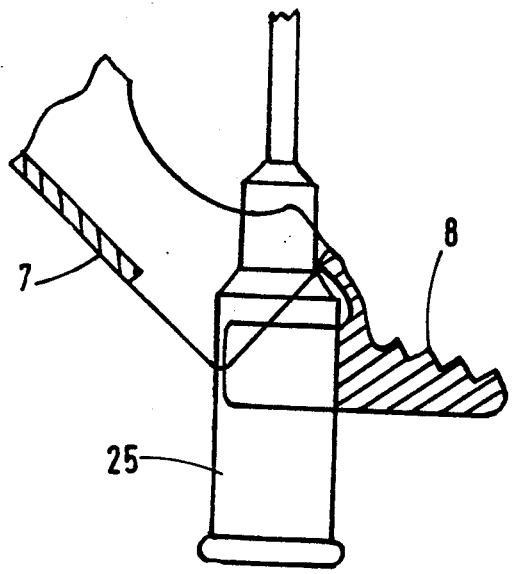
Figure 8F:
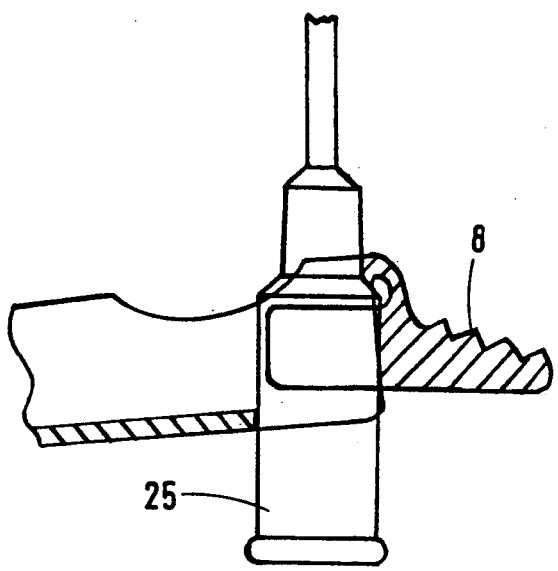
Figure 8G:
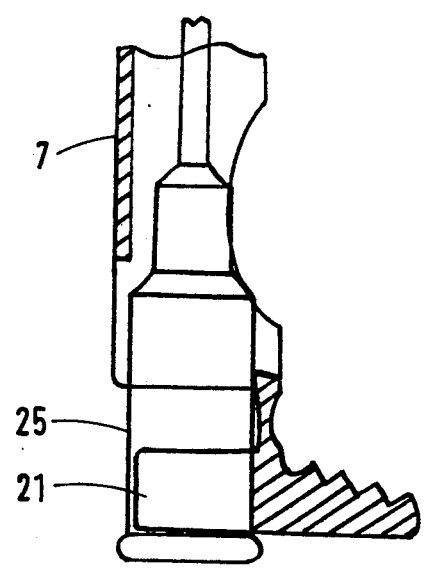
Figure 9A:
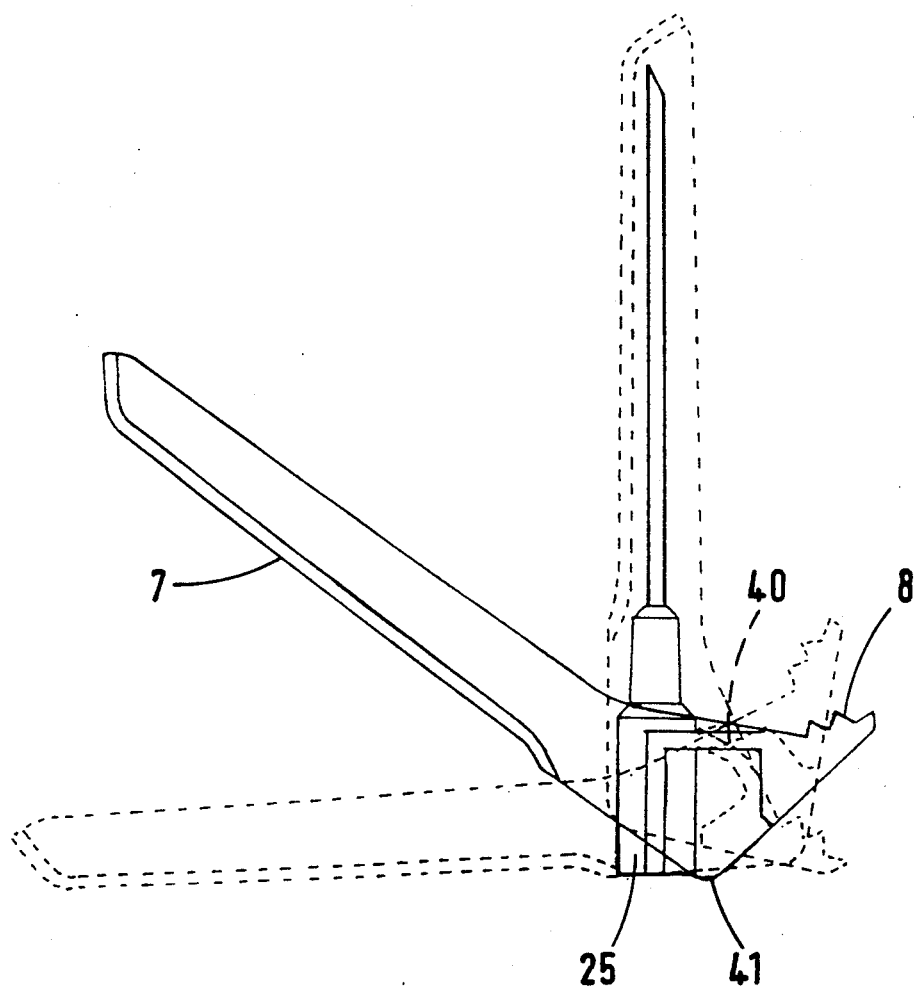

FIG. 2 is a section through the guard and needle showing in solid lines the guard in its first, closed position and in its second, open position in broken lines, FIG. 3 is a section similar to FIG. 2, FIG. 3A is a section through the guard, FIG. 4 is a section taken on the line A—A in FIG. 3, FIG. 5 is a perspective view of the needle assembly with the guard removed, FIG. 5A is a perspective view (partly sectioned) of the guard, FIGS. 6A to 6D are various views of a second embodiment of the invention which includes an integrally moulded sleeve for attachment to a needle boss, FIGS. 7A to 7C are views of a third embodiment of the invention in which the needle guard includes an integrally moulded needle boss, FIGS. 8A to 8G are several views of a fourth embodiment of the invention, FIGS. 8E to G illustrating its operation, FIGS. 9A to 9N are views of a fifth embodiment of the invention in which the needle guard is moulded integrally with the needle boss.

Referring to the drawings and particularly, FIG. 1, the needle and guard assembly comprises a needle 1 of standard design and dimensions which is supported by a moulded plastics boss 2. Boss 2 is generally of standard form in so far as it is designed to be fitted at its lower portion 4 to a conventional hypodermic syringe barrel (not shown) and is sealed to the lower end 3 of the hollow needle 1 in an upper portion 5 of reduced diameter (see FIG. 4). Moulded to the outside of base portion 4 is a pair of trunnions 6 on which a needle shroud 7 is pivotally mounted and constitutes the effective part of the guard.

Shroud 7 (and also needle boss 2) are preferably injection moulded from a thermoplastics material. As best seen in FIG. 1, shroud 7 has a generally trough-shaped form and in its closed position, shrouds the needle on three sides and covers the tip.

An extension arm 8 is integrally moulded with the main body of the shroud 7 and facilitates pivoting of the guard from its open, operative position as shown in broken lines in FIG. 2, to its closed, protective position, shown in solid lines in FIG. 2.

Locking of the shroud in the open and closed positions may be achieved by cooperating features moulded in the shroud 7 and the boss 2. These may take the form of projections moulded on one of these components which engage with a corresponding recess in the other component. Thus, the shroud 7 may be moulded with a projection 9 which is adapted to be a snap fit into a corresponding recess 10 formed in the boss when the shroud is pivoted into the closed position. Similarly, the shroud may be moulded with a similar projection 11 which is adapted to form a snap fit with a recess 12 when the shroud is pivoted into its open position.

It will be appreciated that other devices may be moulded to the shroud and/or needle boss to retain the guard in the closed and operative positions. For example, the walls of the shroud may be tapered in thickness so that when pivoted in one position, the shroud is pressed more tightly against the boss.

It may also be desirable to provide some means to prevent re-use of the syringe. This may be achieved, for example, by moulding a resilient finger or fingers to the inside faces of the shroud. The finger is normally trapped between the boss and the inner wall of the shroud but when the shroud is closed and pivoted into an 'over-centre' position, the finger is released and engages with a recess in the boss, thus preventing removal of the guard and re-use of the needle.

As best seen in FIG. 5A, the guard is moulded with holes 13 to receive trunnions 6 and a tapered lead slot 14 so that in manufacture the moulded shroud 7 can be pushed onto the trunnions 6. A thermoplastics material is chosen which has sufficient flexibility that the trunnions will ride up the lead slot 14 and snap into holes 13.

After assembly of the guard onto the needle, the resulting assembly may be packaged in a sterile pack, such as a shrink-wrap film, and provided with a tear-strip to ease removal of the film prior to use.

FIG. 6A is a perspective view of an embodiment in which the needle guard is moulded integrally with a sleeve which is adapted to fit over a needle boss. The needle shroud portion 7 has an operating arm 8 attached to one side by a flexible strap 20. On the side remote from strap 20, shroud 7 is attached to a sleeve 21 by a plastic hinge 22. The end of arm 8 remote from shroud 7 is also attached by a flexible hinge 23 to second sleeve 24. Sleeves 21 and 24 are internally shaped and dimensioned so that they fit over a standard needle boss and are anchored tightly thereon. As shown in FIG. 6D, the elements of the guard are flexibly interconnected and can be readily manufactured as a single moulding, e.g. by injection moulding.

FIGS. 6B and 6C show the manner in which the guard is operated. The guard is desirably packaged together with the needle and its attached boss in the manner shown in FIG. 6C. A syringe body can then be attached to the needle boss in the usual way and any packaging film or outer packaging removed from the needle guard/needle assembly. Needle shroud 7 is then gripped and pivoted into the position shown in FIG. 6B. In this position, the syringe is filled with the medication to be administered and the injection given or the sample taken from the patient. At this stage, the tip of the needle is contaminated with blood and the needle shroud 7 is snapped back into the guarded position shown in FIG. 6C by downward thumb pressure on the arm 8 without any risk of touching the tip. The guarded needle can then be discarded safely while the tip continues to be protected by the shroud 7. Strap 20 is provided with a slot and opening 26 into which the upper part of the boss 25 engages when the needle shroud is in its open position (FIG. 6B), so as to hold the shroud steady in this position. Similarly, the lower part of the needle shroud may be shaped so as to engage the needle boss in the closed position. One or more corresponding protrusions and recesses 27 and 28 may be formed on the sleeves 21 and 24 in order to inhibit twisting of the sleeves on the needle boss.

FIGS. 7A, B and C illustrate a modification of the embodiment of FIGS. 6A, B, C and D in which the main difference is that a needle boss is moulded integrally as part of the guard. The same reference numerals are used to indicate parts in this embodiment which are the same of similar to those in the FIG. 6A embodiment. FIG. 7A shows the needle guard in the initial and final closed positions in full lines and in its open position in broken lines. The method of operating the needle guard and using the syringe is essentially identical to that described in connection with FIG. 6A, B, C and D. Referring to FIG. 7A, this shows the most convenient configuration for moulding the needle guard. As can be seen, a needle boss 25 is connected by an integral flexible strap 29 to arm portion 8. Needle boss 25 is similar to standard needle bosses except that it incorporates an anchor point 30 for attachment of the integral strap 29. FIG 7C shows in plan view a part of the moulding FIG. 7B. Aperture 26 is connected to slot 26a via a throat which resiliently retains the needle shroud in its open position. The restricted width of the slot 26a compared with diameter 31 also means that there is a resistance to pivoting the needle guard into its open position. This has the effect of providing a resilient biasing against pivoting of the needle guard out of its open or closed positions. In other words, it is necessary to exert a positive pivoting force on the needle shroud to move it from one of its two rest positions, i.e., fully closed and fully opened.

FIGS. 8A, B, C, D, E and F show a further modification of the embodiment shown in FIG. 6A. Again, the same reference numerals are used to indicate corresponding parts. The major difference is that the operating arm 8 is connected to a hinge 32 connected to a forked portion which closes off the base of the open side of shroud 7. In the open position of the shroud shown in FIG. 8C, forked portion 33 lies on the shoulder 34 of needle boss 25. Shroud 7 may be resiliently held in this position by ears 35 engaging over sleeve 21. Downward thumb pressure on arm 8 causes the shroud 7 to return to the closed position by forked portion 33 riding over shoulder 34. This downward pressure on arm 8 causes the sleeve 21 to slide downwardly over boss 25 until the shroud snaps back into the closed position. Because needle bosses are normally tapered, sleeve 21 must usually be broken as shown in FIG. 8A to 35. The sequence of relative movement between the sleeve 21 and the boss 25 is illustrated in FIGS. 8D to 8G. This embodiment also includes at 36, (see FIGS. 8A and 8B), a foam insert in the tip of shroud 7 which is positioned to absorb any drops of blood which may be adhering to the needle tip. If desired, this feature can be included in any of the embodiments.

FIG. 9A shows a further embodiment in which the needle shroud 7 is moulded integrally with a needle boss. Although the moulding is a little more complex in this embodiment, the mechanics of the hinge movement are better than the arrangement shown in FIGS. 6A and 7A and for this reason among others it is currently preferred. In FIG. 9A, the needle shroud 7 is shown in full lines in an intermediate position, between open and closed positions, in which it is conveniently moulded together with a needle boss and interconnecting hinge. As in all embodiments, the needle is sealingly fixed into the boss, e.g. with adhesive or by heat softening the tip of the boss just prior to packaging the needle/guard assembly. FIG. 9A additionally shows in ghosted lines the open and closed positions of the needle shroud. Needle shroud 7 is connected to needle boss 25 by integrally moulded hinge element 40. Because the needle assembly is moulded in its intermediate position, pivoting movement of the shroud in its open position tends to stretch the hinge element and this stress assists the movement of the shroud into its closed position in a smooth action. Also the thumb pressure on the arm 8 is translated into a pulling action, via hinge 40, on the upper end of the needle boss 25. Since the shroud 7 pivots about the heel 41 of the shroud, this action generates a moment equal to appropriately the height of the needle boss which is effective in closing the shroud around the needle.

Figure 9B:
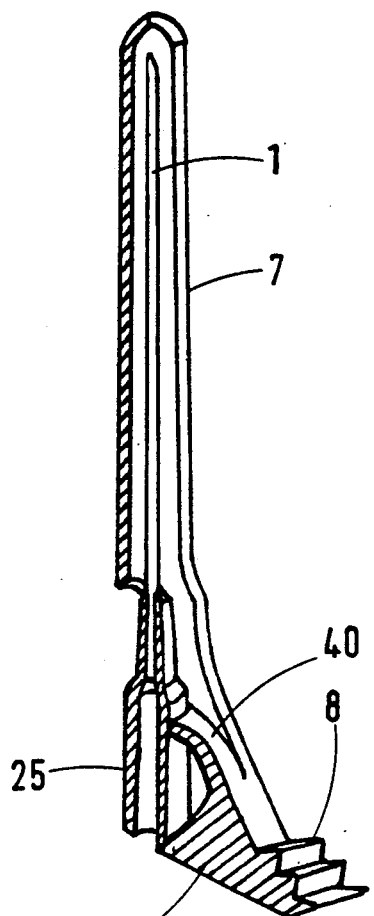
Figure 9C:
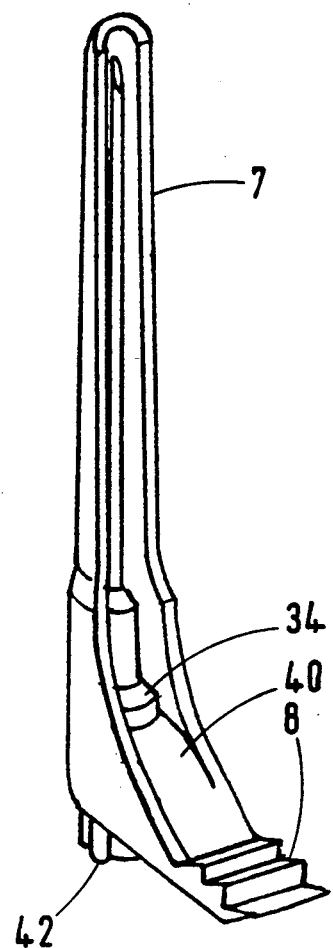

FIG. 9B is a perspective view, partially in section and FIG. 9C is a similar but full perspective view showing the connection of shroud 7 to the needle boss solely by the integrally-moulded hinge or strap 40. The arm 8 is shown as solid plastic, although it will be appreciated that this could be hollowed somewhat to save material.

Figure 9D:
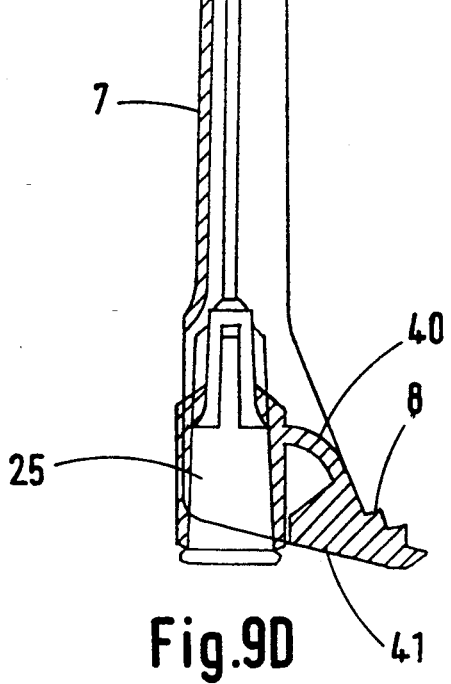

In FIG. 9D, the same embodiment is shown in its closed position in longitudinal section and giving a better view of the shape of the heel portion 41.

Figure 9E:
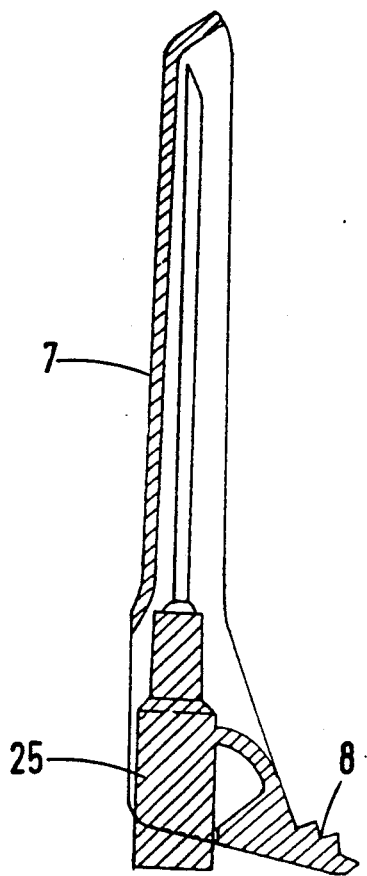
Figure 9F:
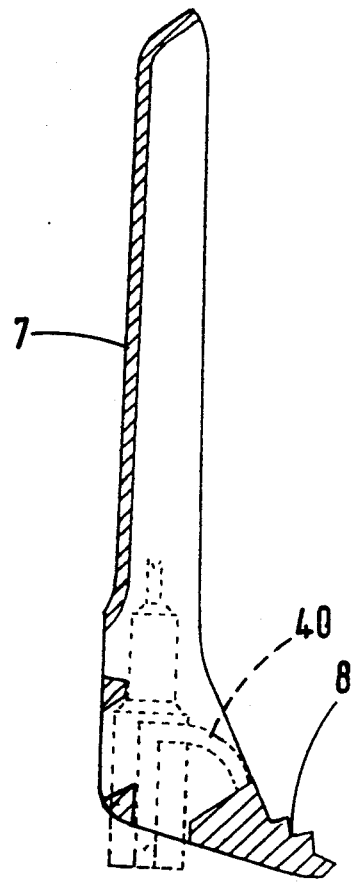
Figure 9G:
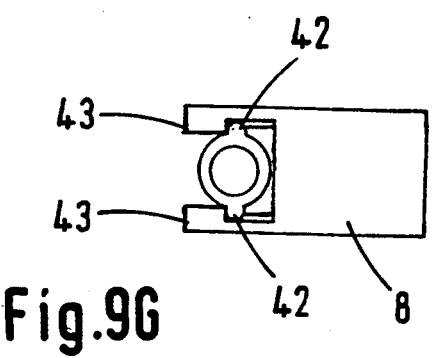
Figure 9H:
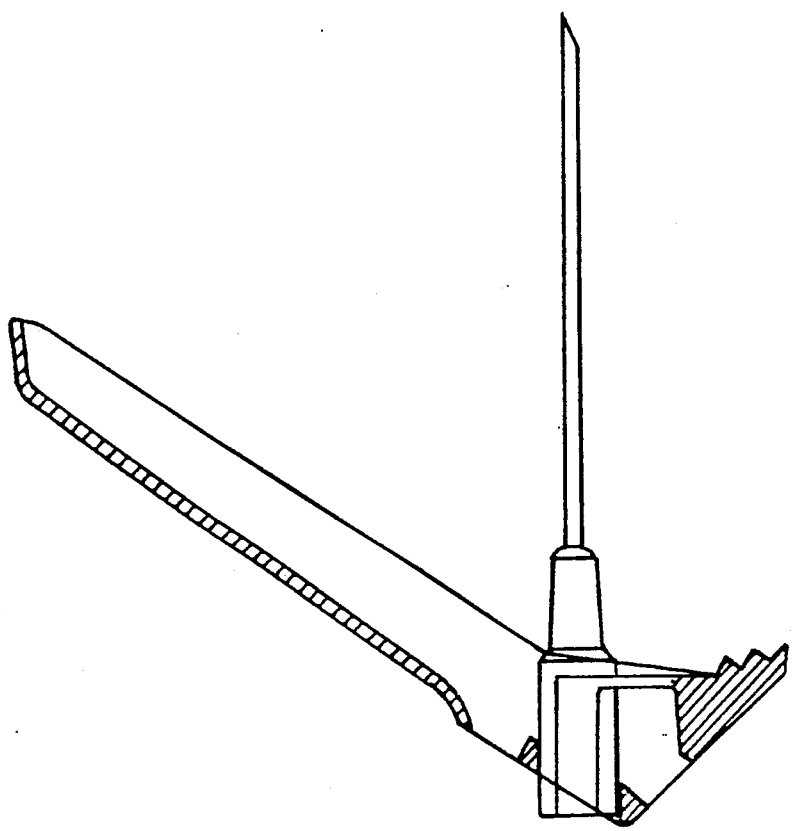
Figure 9J:
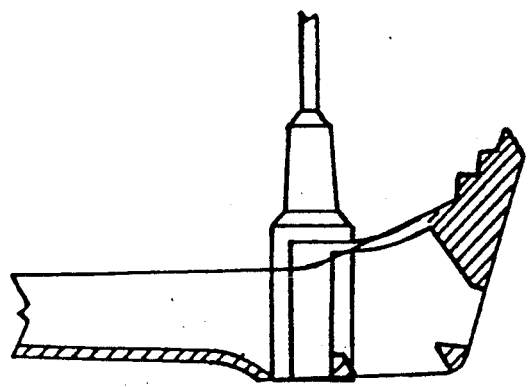
Figure 9K:
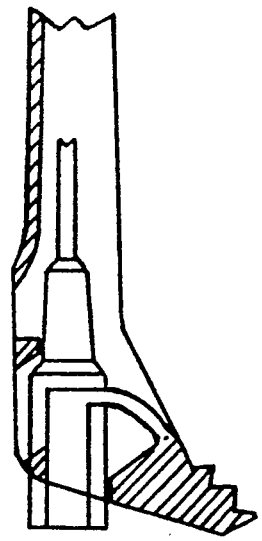
Figure 9L:
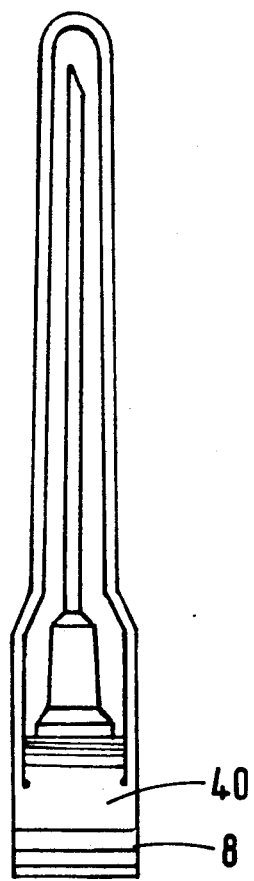
Figure 9M:
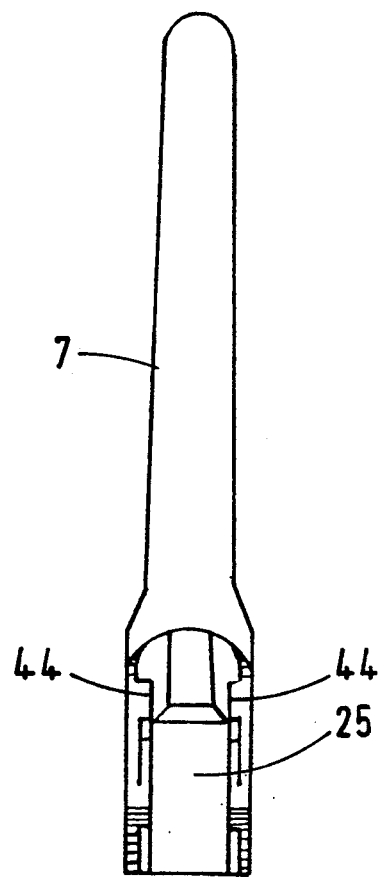

FIGS. 9E and F are longitudinal sections at two different depths through the needle guard assembly and FIG. 9G is a plan view from below. A pair of longitudinal ribs 42 moulded on the outside of the needle boss 25 are clearly apparent in FIGS. 9F to 9G as well as in FIG. 9C. Ribs 42 contact a pair of abutment 43 in the closed position. Abutments 43 are moulded on the inside of shroud 7 and move over ribs 42 when the shroud is pivoted into its open position and accordingly resilient restrain the shroud in the closed position. An additional pair of abutments 44 are moulded on the inside of the shroud in such a position as to engage ribs 42 when the shroud is in its open position and these resiliently hold the shroud steady until the resistance is overcome by pressure on arm 8 to cause the shroud to close. The pivoting movement of the shroud 7 about the needle boss 25 and the engagement of the abutments 43 and 44 with the ribs 42 in the open and closed positions is shown more clearly in FIGS. 9H, 9J and 9K.

FIG. 9N is a further side elevation, partly in section, of the embodiment of Figure in its preferred moulding position and FIG. 9P is a plan view, seen from below, of FIG. 9N. Cross-sectional views taken respectively along the lines 1, 2, 3 and 4 in FIG. 9N are illustrated in FIGS. 9N1, 9N2, 9N3 and 9N4. It will be appreciated from these views that this embodiment can be mounted by using appropriate insert tools, introduced from above and below.

I claim:

1. A hypodermic syringe having a needle guard which is pivotable between a first position in which it covers the tip of the needle and a second position in which the needle tip is exposed and the guard lies in a position which does not interfere with the use of the syringe by finger pressure applied to a lever extension portion of said guard, said guard being moulded integrally with a boss for supporting the needle or with a sleeve which is adapted to be fitted over a needle boss, the needle guard being connected to the needle boss or to said sleeve by a flexible, integrally moulded strap and wherein the guard is connected by a plastic hinge to a second sleeve which is adapted to be fitted over the needle boss.

2. A syringe according to claim 1 in which the guard includes means for releasably holding it in said first and second positions.

3. A syringe according to claim 1 or claim 2 in which the guard comprises a generally through-shaped shroud which is adapted to shroud the needle on three sides and to protect the tip in said first position and in which the shroud is pivotably mounted at the base of the needle so that on pivoting the shroud from said second to said first position, the needle enters the open side of the trough-shaped shroud.

4. A syringe according to claim 1 wherein said strap connects said lever extension portion of the guard to the needle boss or sleeve and wherein flexing of the strap allows the guard to pivot between said first and second positions.

5. A needle assembly for a syringe which comprises a needle boss having a needle projecting therefrom, a needle guard integrally attached to the needle boss by a flexible strap, which includes a guard-operating arm portion, said guard including a shroud portion which, in a first position, is capable of protecting the needle tip and in a second position, allows the needle to be used with a syringe, the flexible strap permitting movement of said guard from said first to said second position and forms a loop with the needle boss so that finger pressure on said arm portion causes return movement of said guard.

6. A needle assembly according to claim 5 which includes integrally moulded engagement means on said guard and/or on said boss for biasing the guard against pivoting out of its open or closed positions.

7. A hypodermic syringe having a needle boss and needle connected to a barrel, a plastic moulded needle guard including an integrally-moulded sleeve for retaining the needle guard on the boss, said guard including a shroud portion which, in a first position is capable of protecting the needle tip and in a second position allows the needle to be exposed and used, the shroud portion being connected to the sleeve portion by a strap portion permitting movement of the shroud portion from said first to said second position and wherein the shroud portion includes an integrally moulded operating lever linked to the sleeve by said strap, whereby finger pressure on said arm portion causes return movement of the shroud portion to said first position.

* * * * *